US00PP37602P2

(12) United States Plant Patent
Heuger

(10) Patent No.: US PP37,602 P2
(45) Date of Patent: Aug. 18, 2026

(54) ***HELLEBORUS* PLANT NAMED 'HL 1064'**

(50) Latin Name: ***Helleborus* x *niger* X *Helleborus* x *hybridus***
Varietal Denomination: HL 1064

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 19/397,972

(22) Filed: Nov. 23, 2025

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'HL 1064', characterized by its upright to outwardly spreading and mounded plant habit; moderately vigorous to vigorous growth habit; dark green-colored leaflets; freely flowering habit; flowers with white to light purple-colored petals and light purplish pink-colored sepals; and good garden performance.

2 Drawing Sheets

Figure 1:
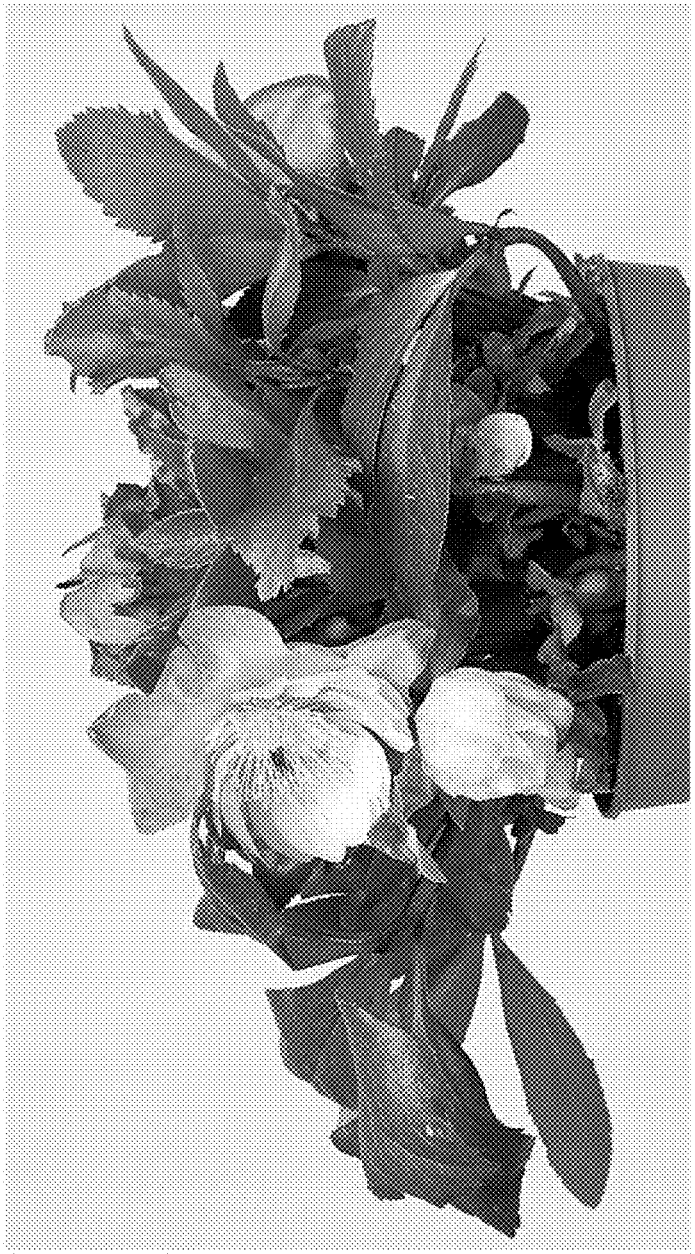

Botanical designation: *Helleborus* x *niger* X *Helleborus* x *hybridus*.

Cultivar denomination: 'HL 1064'.

CROSS-REFERENCED TO CLOSELY-RELATED APPLICATIONS

A European Community Plant Breeder's Rights application for the instant plant was filed by the Inventor/Applicant, Mr. Josef Heuger of Glandorf, Germany, on Nov. 30, 2024, application number 2024/2906. Foreign priority is not claimed to this application.

A United Kingdom Plant Breeder's Rights application for the instant plant was filed by the Inventor/Applicant, Mr. Josef Heuger of Glandorf, Germany, on Aug. 29, 2025, application number 30/986. Foreign priority is not claimed to this application.

BACKGROUND OF THE INVENTION

The present invention relates to a new and distinct cultivar of *Helleborus* plant, botanically known as *Helleborus* x *niger* X *Helleborus* x *hybridus* and hereinafter referred to by the name 'HL 1064'.

The new *Helleborus* plant is a product of a planned breeding program conducted by the Inventor in Glandorf, Germany. The objective of the breeding program was to create new uniform *Helleborus* plants with unique leaf and flower coloration and tolerance to biotic and abiotic stresses.

The new *Helleborus* plant originated from a cross-pollination conducted by the Inventor in Glandorf, Germany in December, 2017 of a proprietary selection of *Helleborus* x *niger* identified as code number 001, not patented, as the female, or seed, parent and a proprietary selection of *Helleborus* x *hybridus* identified as code number 16-27, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2019.

Asexual reproduction of the new *Helleborus* plant by in vitro axillary meristem culture in a controlled environment in Glandorf, Germany since September, 2020 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1064'. These characteristics in combination distinguish 'HL 1064' as a new and distinct *Helleborus* plant:

1. Upright to outwardly spreading and mounded plant habit.
2. Moderately vigorous to vigorous growth habit.
3. Dark green-colored leaflets.
4. Freely flowering habit.
5. Flowers with white to light purple-colored petals and light purplish pink-colored sepals.
6. Good garden performance.

Plants of the new *Helleborus* differ from plants of the female parent selection in the following characteristics:

1. Petals of plants of the new *Helleborus* are not transformed into nectaries whereas petals of plants of the female parent selection are transformed into nectaries.
2. Flower sepals of plants of the new *Helleborus* are light purplish pink in color whereas flower sepals of plants of the female parent selection are white in color.

Plants of the new *Helleborus* differ from plants of the male parent selection in the flower form as flowers of plants of the new *Helleborus* have fewer petals than flowers of plants of the male parent selection.

Plants of the new *Helleborus* can also be compared to plants of *Helleborus* x *niger* X *Helleborus* x *hybridus* 'COSEH 5900', disclosed in U.S. Plant Pat. No. 32,340. In side-by-side comparisons, plants of the new *Helleborus* differ primarily from plants of 'COSEH 5900' in the following characteristics:

1. Petals of plants of the new *Helleborus* are not transformed into nectaries whereas petals of plants of 'COSEH 5900' are transformed into nectaries.
2. Flower sepals of plants of the new *Helleborus* are light purplish pink in color whereas flower sepals of plants of 'COSEH 5900' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1064' grown in a container.

Figure 2:
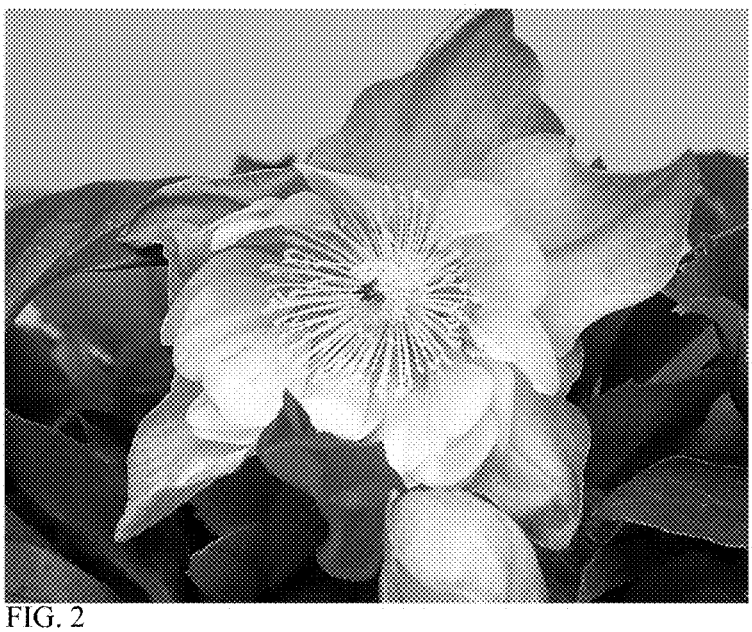

The photograph at the top of the second sheet (FIG. 2) is a close-up view of a typical flower of 'HL 1064'.

Figure 3:
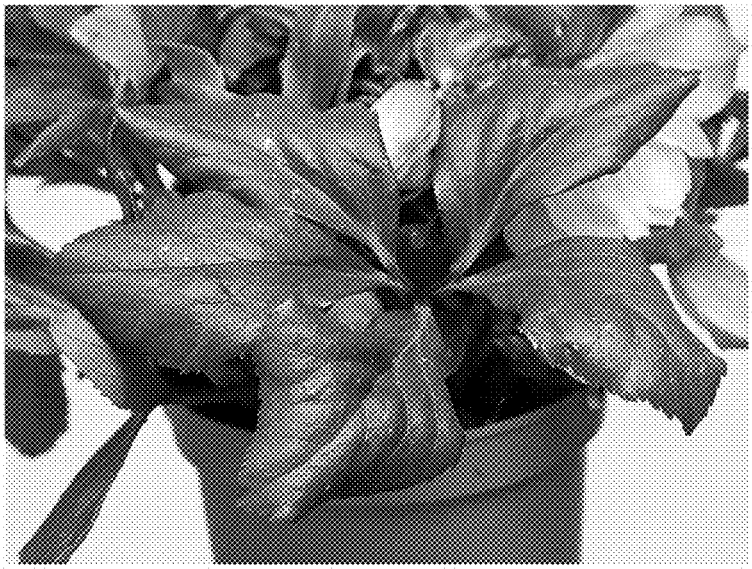

The photograph at the bottom of the second sheet (FIG. 3) is a close-up view of typical leaflets of 'HL 1064'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 48 weeks old when the photographs were taken and 14 months old when the detailed description was taken. In the following description, color references are made to The Royal Horticultural Society Colour Chart, Sixth Edition (2019 reprint), except where general terms of ordinary dictionary significance are used.

Botanical classification: *Helleborus* x *niger* X *Helleborus* x *hybridus* 'HL 1064'.

Parentage:

*Female, or seed, parent*.—Proprietary selection of *Helleborus* x *niger* identified as code number 001, not patented.

*Male, or pollen, parent*.—Proprietary selection of *Helleborus* x *hybridus* identified as code number 16-27, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to outwardly spreading and mounding plant habit with flowers held above the foliar plane; plant shape, roughly flattened globular to globular; moderately vigorous to vigorous growth habit and moderate growth rate.

*Plant height, soil level to top of foliar plane*.—About 20.1 cm.

*Plant height, soil level to top of flowers*.—About 20.4 cm.

*Plant diameter* (*area of spread*).—About 40.4 cm.

Leaf description:

*Arrangement*.—Leaves arranged in basal rosettes; leaves palmately compound with typically five leaflets per leaf.

*Leaf length*.—About 14.6 cm.

*Leaf width*.—About 17.4 cm.

*Leaflet length*.—About 10.3 cm.

*Leaflet width*.—About 4.9 cm.

*Leaf shape*.—Palmate; roughly reniform in outline.

*Leaflet shape*.—Ovate to elliptic; slightly convex; occasionally, the lowest leaflets are cleft.

*Leaflet apex*.—Acute to bluntly acute.

*Leaflet base*.—Attenuate.

*Leaflet margin*.—Serrate; slightly coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; slightly to moderately glossy.

*Leaflet venation pattern*.—Pinnate and reticulate.

*Leaflet color*.—Developing leaflets, upper surface: Close to 137B; at the base, close to 183A. Developing leaflets, lower surface: Close to 138B; main veins, close to 178A. Fully developed leaflets, upper surface: Close to a blend of NN137A and 147A; at the base, tinged with close to 200B; venation, close to 143B. Fully developed leaflets, lower surface: Close to a blend of 137B and 147B; venation, close to 146C.

*Petioles*.—Length: About 13.1 cm. Diameter: About 6 mm by 7 mm. Strength: Strong. Texture and luster, upper and lower surfaces: Smooth, glabrous; slightly glossy. Color, upper surface: Close to 146C with fine dots, close to 200C. Color, lower surface: Close to 146D with fine dots, close to N199B.

Flower description:

*Flower shape and habit*.—Double rotate bowl-shaped flowers arranged in panicles; freely flowering habit with about three flowers per inflorescence and about 45 flowers and flower buds per plant; flowers face outwardly to slightly nodding.

*Fragrance*.—None detected.

*Natural flowering season*.—Plants begin flowering about ten months after planting; plants flower naturally from early winter into the late winter in Germany.

*Flower longevity on the plant*.—About ten days; sepals persistent, other flower parts are not persistent.

*Flower buds*.—Length: About 2.2 cm. Diameter: About 1.4 cm. Shape: Ovate. Texture and luster: Smooth, glabrous; matte. Color: Upper surface, close to 145D and 150D tinged with close to 182B; lower surface, close to 145D and 150D.

*Inflorescence height* (*including peduncle*).—About 20.2 cm.

*Inflorescence diameter*.—About 11.7 cm.

*Flower diameter*.—About 9.8 cm.

*Flower depth*.—About 3.2 cm.

*Petals*.—Quantity and arrangement: About 15 to 18, arranged in a single whorl. Length: About 3.7 cm. Width: About 1.4 cm. Shape: Elliptic. Apex: Bluntly acute. Base: Attenuate. Margin: Entire; not undulate. Texture and luster, upper surface: Smooth, glabrous; matte. Texture and luster, lower surface: Smooth, glabrous; slightly glossy. Color: When opening, upper surface: Close to NN155D; at the base, close to 145B to 145C. When opening, lower surface: Close to NN155D slightly tinged with close to 75C; at the base, close to 145B to 145C. Fully opened, upper surface: Close to N155B tinged with close to 75C; at the base, close to 145B; venation, close to 75C; with subsequent development, color becoming closer to 75D, tinged towards the margins with close to 76C, tinged towards the apex with close to 151D, and at the base, close to 144B. Fully opened, lower surface: Close to NN155B slightly tinged with close to 75C; at the base, close to 145B; venation, close to 75C; with subsequent development, color becoming closer to 75D, tinged towards the apex, margins and base, close to 76C and at the base, close to 144B.

*Sepals*.—Quantity and arrangement: About five, arranged in a single whorl. Length: About 5.2 cm. Width: About 4.3 cm. Shape: Broadly elliptic to broadly ovate; slightly concave. Apex: Broadly and bluntly acute to obtuse. Base: Cuneate. Margin: Entire. Texture and luster, upper surface: Smooth, glabrous; matte. Texture and luster, lower surface: Smooth, glabrous; slightly glossy. Color, upper sepals: When opening, upper surface: Close to 69D; towards the apex and base, slightly tinged with close to 75D; marginal edges, close to 69D; at the base, close to 145B. When opening, lower surface: Close to 69D; towards the apex, slightly tinged with close to 75C; towards the base, tinged with close to 186B; marginal edges, close to 69D; at the base, close to 145B. Fully opened, sepals, upper surface: Close to 69D; towards the apex, tinged with close to N66C; at the base, close to 145C. Fully opened, lower surface: Close to 69D; towards the apex, close to 186B; towards the base, tinged with close to 185C and 185D; at the base, close to 146D. Color, lower sepals: When opening, upper surface: Close to 69D; towards the apex and base, slightly tinged with close to 75D; marginal edges, close to 69D; at the base, close to 145B. When opening, lower surface: Close to 69D; towards the apex, slightly tinged with close to 75C; towards the base, tinged with close to 186B; marginal edges, close to 69D; at the base, close to 145B. Fully opened, sepals, upper surface: Close to 69D; towards the apex, close to 186A and tinged with close to 146C; at the base, close to 145C. Fully opened, lower surface: Close to 69D; towards the apex, close to 186A tinged with close to 146A and 146B; towards the base, tinged with close to 185C and 185D; at the base, close to 146D.

*Flower bracts*.—Quantity per flower: Typically one or two. Length: About 7.9 cm. Width: About 4.7 cm. Shape: Ovate to obovate. Apex: Acute. Base: Truncate to cuneate. Margin: Entire and distally, serrate; coarsely undulate. Color, upper surface: Close to 137A. Color, lower surface: Close to 138B; main vein, tinged with close to 187C.

*Peduncles*.—Length: About 12.1 cm. Diameter: About 6 mm to 7 mm. Aspect: About 15° from vertical. Strength: Strong. Texture and luster: Smooth, glabrous; moderately glossy. Color: Close to 146D; heavily covered with fine dots, close to 187B.

*Pedicels*.—Length: About 4.5 cm. Diameter: About 4 mm. Aspect: About 15° from peduncle axis. Strength: Moderately strong. Texture and luster: Smooth, glabrous; moderately glossy. Color: Close to 145B; heavily covered with fine dots, close to 182C.

*Reproductive organs*.—Stamens: Quantity per flower: About 120.Filament length: About 2.1 cm. Filament color: Close to 155B. Anther shape: Double and broadly reniform; basifixed. Anther size: About 2 mm by 3 mm. Anther color: Close to 154C. Pollen amount: Sparse. Pollen color: Close to 4D. Pistils: Quantity per flower: About five to eight. Pistil length: About 1 cm. Stigma diameter: About 0.3 mm. Stigma shape: Club-shaped. Stigma color: Close to 155C. Style length: About 0.95 cm. Style color: Close to 184A. Ovary color: Close to 154D. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1064' as herein illustrated and described.

* * * * *